United States Patent [19]

Saito et al.

[11] Patent Number: 4,681,513
[45] Date of Patent: Jul. 21, 1987

[54] TWO-STAGE PUMP ASSEMBLY

[75] Inventors: Toshinori Saito; Makoto Takeuchi, both of Tokyo, Japan

[73] Assignee: Jeol Ltd., Tokyo, Japan

[21] Appl. No.: 823,341

[22] Filed: Jan. 28, 1986

[30] Foreign Application Priority Data

Feb. 1, 1985 [JP] Japan .................................. 60-18437
Feb. 1, 1985 [JP] Japan ............................ 60-13150[U]

[51] Int. Cl.⁴ ..................... F04B 41/06; F04B 49/06; F04B 3/00
[52] U.S. Cl. .......................................... 417/2; 417/18; 417/45; 417/63; 417/265
[58] Field of Search ................... 417/2, 18, 45, 53, 63, 417/265

[56]  References Cited

U.S. PATENT DOCUMENTS

| 4,137,011 | 1/1979 | Rock .................... 417/53 X |
| 4,225,290 | 9/1980 | Allington .............. 417/18 |
| 4,236,877 | 12/1980 | Curtis .................... 417/265 |
| 4,321,014 | 3/1982 | Eburn, Jr. et al. ....... 417/53 X |
| 4,352,636 | 10/1982 | Patterson et al. ....... 417/265 X |
| 4,359,312 | 11/1982 | Funke et al. ............ 417/18 |
| 4,389,163 | 6/1983 | Magnussen, Jr. et al. ... 417/265 X |
| 4,552,513 | 11/1985 | Miller et al. ........... 417/265 X |
| 4,556,367 | 12/1985 | Schmid ................... 417/265 X |
| 4,600,365 | 7/1986 | Riggenmann .............. 417/265 X |

FOREIGN PATENT DOCUMENTS 1534650 12/1978 United Kingdom ................ 417/265

Primary Examiner—Carlton R. Croyle
Assistant Examiner—Paul F. Neils
Attorney, Agent, or Firm—Webb, Burden, Robinson & Webb

[57]  ABSTRACT

An accurately controllable two-stage pump assembly comprising two plunger pumps connected in series. The suction port of the outlet pump A is connected to the discharge port of the inlet pump B, so that the discharge port of the outlet pump A and the suction port of the inlet pump B act as the discharge port and the suction port, respectively, of the whole pump assembly. While the inlet pump B is delivering fluid from the whole pump assembly, the outlet pump A completes the filling stroke of the whole pump assembly and fully increases the pressure inside the chamber of the outlet pump A. While the inlet pump B is filling, the outlet pump A is in the stage of displacement stroke and delivers fluid from the whole pump assembly. The plungers of the pumps are moved via cams by stepper motors which swing or rotate back and forth within a certain angular range.

5 Claims, 14 Drawing Figures (a)

(b)

TWO-STAGE PUMP ASSEMBLY

DESCRIPTION

BACKGROUND OF THE INVENTION

The present invention relates to an improved two-stage pump assembly for use in a liquid chromatograph or other instrument.

Some instruments must deliver fluid, such as liquid and liquefied gas, at a constant flow rate. For example, a liquid chromatograph uses a pump that delivers fluid to a column or introduces a sample at a constant flow rate. Double plunger pumps of the structure as shown in FIG. 1 are often employed for such purposes. For the operation of the double plunger pump, see U.S. Pat. No. 4,436,230.

Referring to FIG. 1, a pump assembly is mounted on a support 1. Plunger pumps 2 and 3 have cylinders 4 and 5, respectively, which are mounted to the support 1. Plungers 6 and 7 are fitted in the cylinders 4 and 5, respectively. As the plungers reciprocate, the volumes of the chambers 8 and 9 of the cylinders are changed. Check valves 10 and 11 are mounted at the suction port and the discharge port, respectively, of the chamber 8, and check valves 12 and 13 are mounted at the suction port and the discharge port, respectively, of the chamber 9, to allow fluid to pass only in the direction indicated by the arrows. A pipe 17 is connected to the valves 11 and 13 mounted at the suction ports, and is immersed in a fluid (sample) 14 contained in a reservoir 15, the fluid 14 being under the atmospheric pressure. A pipe 18 which is connected to the valves 10 and 12 mounted at the suction ports is coupled to the separation column of a liquid chromatograph 16. An electric motor 19 is mounted on the support 1 and has its shaft 20 fixed to cams 21 and 22 that allow the plungers 6 and 7 to be moved at constant velocity as described later. Rotors 23 and 24 attached to ends of the plungers 6 and 7, respectively, are always pressed against the sides of the cams 21 and 22, respectively, by the resilient force of springs 25 and 26, respectively. The spring 25 is inserted between the jaw of the plunger 6 and the cylinder 4. Similarly, the spring 26 is inserted between the jaw of the plunger 7 and the cylinder 5.

FIGS. 2(a) and 2(b) show the cams 21 and 22, respectively, installed in the assembly shown in FIG. 1 as viewed from the direction of the axis of the shaft 20, which is taken as Y axis. The cams 21 and 22 are identically shaped into the form of a heart, and are symmetrical with respect to an axis, for example Z axis, perpendicular to the Y axis. The cams 21 and 22 mounted to the shaft 20 are spaced 180° from each other. The rotors 23 and 24 of the plungers bear on the sides of the cams 21 and 22, respectively, at points 27 and 28, respectively. As the motor shaft 20 is rotated, the points 27 and 28 move right and left on the X axis. When the shaft 20 is rotated to the right as indicated by the arrow in FIG. 2 by the motor 19, the plungers 6 and 7 are moved in opposite directions along the X axis. That is, the plunger 6 moves to the right, while the plunger 7 shifts to the left as viewed in FIG. 1. The cam profile of the heart-shaped cams 21 and 22 is so made that the plungers move at constant velocity as long as the rotational velocity of the motor 19 is constant. In this way, while the plunger 6 or 7 travels to the right, the volume of the chamber 8 or 9 increases, closing the valve 10 or 12 at the discharge port. At the same time, the valve 11 or 13 is opened at the suction port. As a result, the sample 14 is drawn into the pump. On the other hand, while the plunger moves to the left, the volume of the chamber 8 or 9 decreases, closing the valve 11 or 13 at the suction port. Simultaneously, the valve 10 or 12 at the discharge port is opened. Thus, the fluid is delivered to the separation column of a liquid chromatograph 16 from the pump chamber.

Since the plungers 6 and 7 move in 180° out-of-phase relationship as mentioned previously, the chamber 8 first takes in the liquid and, at the same time, the chamber 9 pumps the liquid out of it under the condition shown in FIG. 2. Subsequently, the chamber 8 delivers and the chamber 9 fills at the same time. These operations are illustrated in FIG. 3, where time or the angular position of the cam 21 or 22 is plotted on the horizontal axis and the displacements of the plungers 6 and 7 on the vertical axis. The displacement of each plunger is defined as the distance between the point of the plunger 27 or 28 at which it is in contact with the roller and the fundamental circle 29 (FIG. 2) of the cam. The displacement of the plunger 6 is indicated by the solid line, whereas the displacement of the plunger 7 is denoted by the broken line. SA1 and SA3 indicate suction strokes of the chamber 8; SB1 and SB3 indicate displacement strokes of the chamber 9; SA2 and SA4 indicate displacement strokes of the chamber 8; and SB2 and SB4 indicate suction strokes of the chamber 9. If the rotational velocity of the motor is increased to increase the translating velocity of the plunger, then the gradients of the straight lines shown in FIG. 3 become steeper, increasing the amount of fluid displaced per unit time. Usually, this amount is simply known as flow rate, which is proportional to the pressure at the discharge port of the pump.

Referring next to FIG. 4, there are shown changes in the flow rate of the pump assembly shown in FIG. 1 with time. The solid lines represent the flow rate due to the displacement stroke of the first pump chamber. The broken lines indicate the flow rate attributed to the displacement stroke of the second pump chamber. If the flow rate were completely constant, then these solid and broken lines should be parallel to the horizontal axis, or time. Usually, however, the flow line experiences flow resistance, and therefore the delivery pressure is higher than the atmospheric pressure. Immediately after the pump is switched from one filling stroke to its next stroke of displacement, the pressure inside the pump chamber is equal to the atmospheric pressure, so the valve at the discharge port does not open and the liquid is not delivered during a short time that ends when the pressure inside the pump reaches the higher delivery pressure. In this way, the plunger compresses the liquid while the pressure inside the pump chamber varies from the atmospheric pressure to the delivery pressure. This compressing action is absorbed by the compression of the liquid itself and by deformation of the materials sealing the pump chamber. This absorption results in the flow rate of the pumps 2 and 4 to drop, as indicated by 32 in FIG. 4.

Where the analytical column of a liquid chromatograph is connected to the discharge port, if the flow rate of the pump varies or drops as shown in FIG. 4, the base line of the obtained spectrum will pulsate, making accurate measurement impossible. This phenomenon becomes conspicuous especially where a load having a large fluid resistance is connected to the discharge port of the pump, or where a fluid having a large compressibility, such as liquefied gas, is used. Accordingly, the actual average flow rate including flow rate pulsations is lower than the average flow rate that is obtained by calculation without taking into account the aforementioned absorption of the compression action. This makes it very difficult to accurately control the flow rate of the pump to a desired value. A conventional solution to this difficulty is to forecast the effect of the absorption of the compression action and to remove the effect. This scheme is realized by a system as shown in FIG. 5, where the conventional double plunger pump already described in connection with FIG. 1 is indicated by numeral 33. Liquid sample 14 contained in reservoir 15 is drawn into the suction port of the pump 33 via a pipe. A flow resistor 34 is connected to the discharge port of the pump 33. A pipe extends from the exit of the resistor 34 into the atmosphere. A measuring vessel 35 is placed below this pipe. A means 36 for measuring pressure is installed between the discharge port of the pump 33 and the flow resistor 34. In the operation of this system, the pump 33 is driven at a constant rate. The resistance value of the flow resistor 34 is varied successively from zero to a high value. At each resistance value the pressure and the flow rates are measured. The calibration curve shown in FIG. 6 was derived in this way. The flow rate is determined by measuring the volume of the liquid sample 14 stored in the vessel 35 per unit time. The calibration curve indicates that when the pressure at the discharge port of the pump is $P_0$, the actual flow velocity is 0.8 times as high as the flow velocity obtained when the discharge port of the pump is under the atmospheric pressure. Therefore, the decrease in the flow rate can be compensated by increasing the rotational velocity of the motor by a factor of 1/0.8. However, this method introduces the following problems: (1) The calibration curve varies among fluids to be delivered; (2) The calibration curve described above must be prepared for each individual pump; (3) Since the volume of pump absorbed as described above depends on the performance of the components of the pump, the calibration curve varies with time.

One means to moderate the decrease in the average flow rate due to the higher delivery pressure is to lengthen the stroke of the plunger, which increases the maximum volume Q of the pump chamber. Thus, for a certain flow rate the period of movement of the plunger is extended. In other words, the period of the reciprocating motion increases. As a result, the frequency of absorptions of the compressing action per unit time is reduced. Also, since the volume q absorbed as mentioned above is maintained substantially constant irrespective of the maximum volume Q of the pump chamber, the decrease in the average flow rate due to the higher delivery pressure can be held down to a low value. However, if the period of the displacement of plunger, or the period of the occurrence of flow rate pulsations, is increased to an extremely large value, say 1 minute, then normal function of the load on the pump to smooth out flow rate pulsations or the function of a damper for removing pulsations will become inoperative. A further consideration is that, in general, as the period of the reciprocating motion of a pump increases, it becomes impossible or more difficult to continuously change the flow rate of the pump.

Recently, it has been often required that pumps for use in analytical instruments deliver fluid at quite small flow rates. The minimum controllable flow rates needed for normally adopted analytical regions are as follows:

(I) microanalysis—0.1 $\mu$l/min.
(II) semimicroanalysis—1 $\mu$l/min.
(III) macroanalysis—10 $\mu$l/min.

Unfortunately, it is quite difficult to cover these three ranges of flow rates by the use of the pump assembly shown in FIG. 1, where the cams are rotated in one direction to drive the plungers, because if the cams were designed to accommodate any one of the flow rate ranges, then the rotational velocity of the stepper motor for rotating the cams would have to be set to such a high value that the plungers cannot easily follow them; or inversely the velocity of the stepper motor would have to be so slowed down that it can no longer rotate smoothly.

SUMMARY OF THE INVENTION

It is a main object of the present invention to provide a pump assembly equipped with a mechanism for preventing the average flow rate from dropping, which would otherwise be caused by higher delivery pressure of the pump assembly.

It is another object of the invention to provide a pump assembly producing only a small amount of flow rate pulsations.

It is a further object of the invention to provide a pump assembly whose flow rate can be varied without making the period of flow rate pulsations very long.

It is a still further object of the invention to provide a pump assembly capable of delivering fluid over a quite wide range of flow rates.

It is a yet further object of the invention to provide a pump capable of delivering a trace of fluid having a large compressibility, such as liquefied gas, with the same accuracy as ordinary liquids.

These objects are achieved in accordance with the teachings of the invention by a two-stage pump assembly comprising plunger pumps A and B, the suction port of the pump A being connected to the discharge port of the pump B. Thus, the discharge port of the pump A and the suction port of the pump B act as the discharge port and the suction port, respectively, of the whole pump assembly. When the pump B is delivering fluid from the whole pump assembly, the pump A fills and fully elevates the pressure inside the pump A. When the pump B is in the filling stage, the pump A is in the displacement stage and pumps fluid out from the whole pump assembly.

Other objects and features of the invention will become more apparent in the following description and the accompanying drawings in which like numerals refer to like parts.

DESCRIPTION OF THE PREFERRED EMBODIMENT

Figure 1:
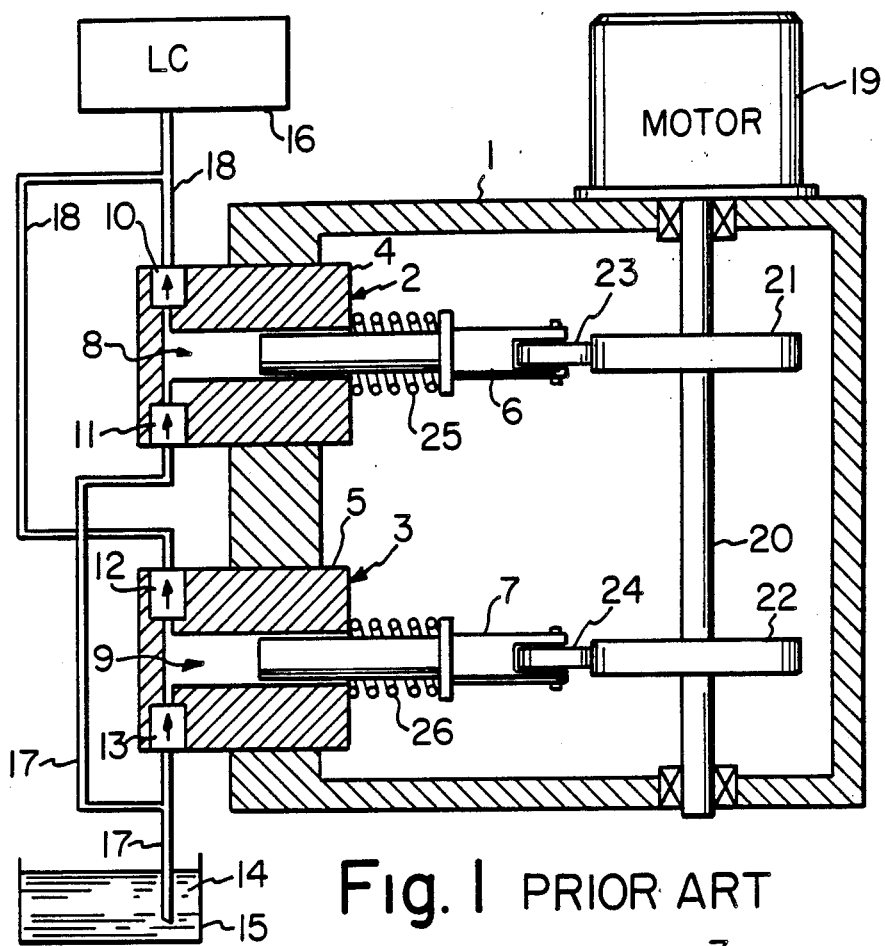
FIG. 1 is a schematic front elevation in cross section of a conventional double plunger pump assembly.
Figure 2:
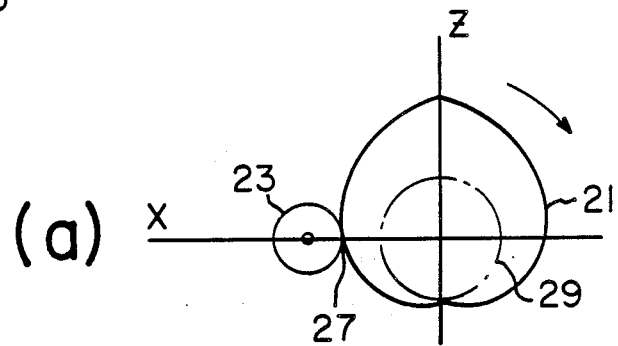
FIGS. 2(a) and 2(b) schematically shows portions of the assembly shown in FIG. 1.
Figure 2:
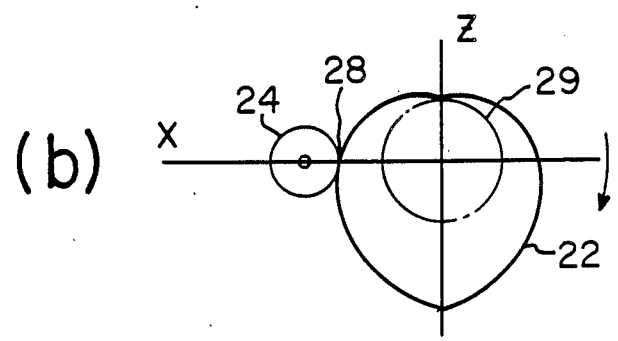
Figure 3:
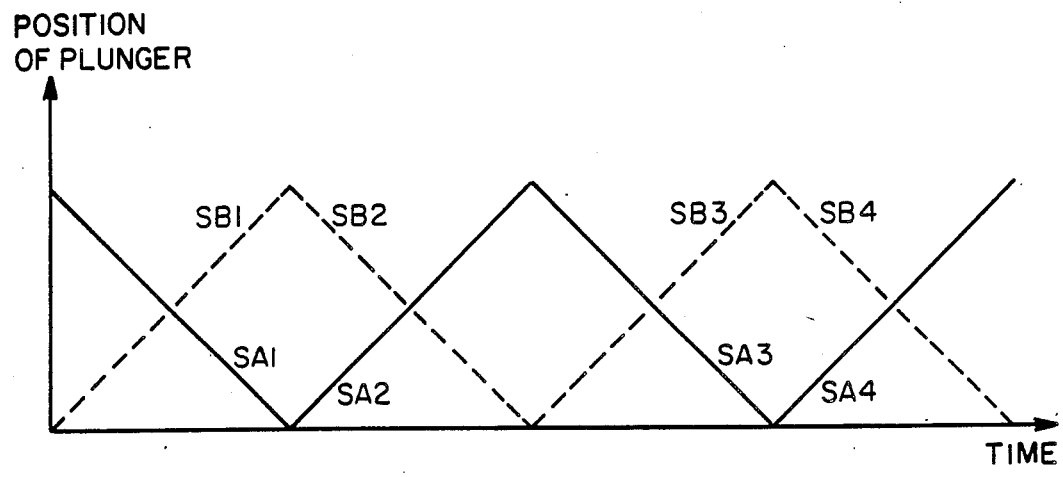
FIGS. 3 and 4 are graphs for illustrating the operation of the pump assembly shown in FIG. 1.
Figure 4:
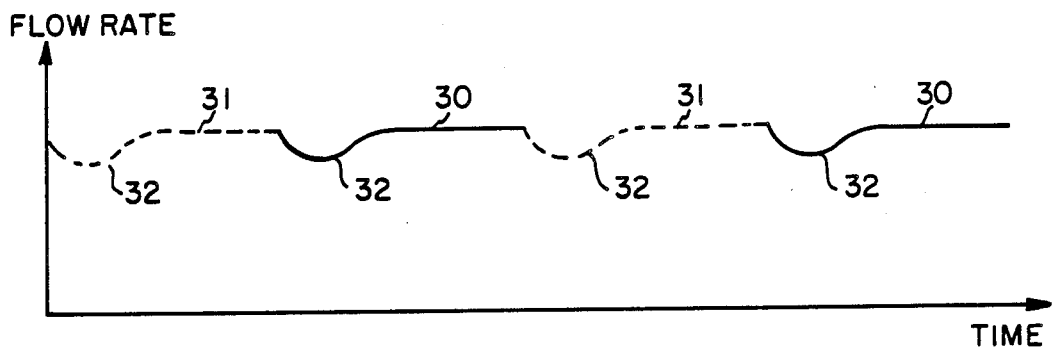
Figure 5:
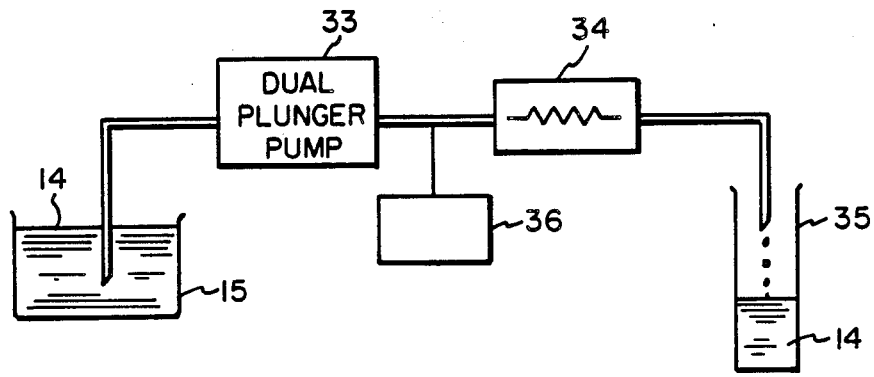
FIG. 5 is a schematic view of a system for obtaining a calibration curve in accordance with the prior art procedures.
Figure 6:
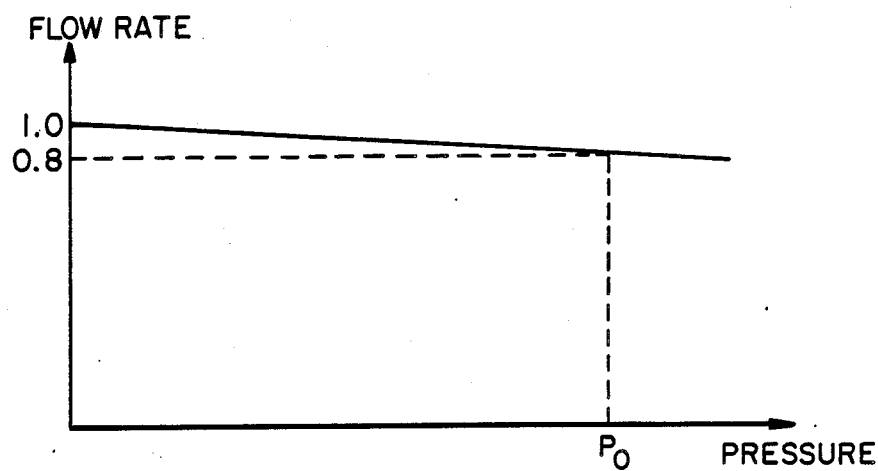
FIG. 6 is a graph obtained by the system shown in FIG. 5.
Figure 7:
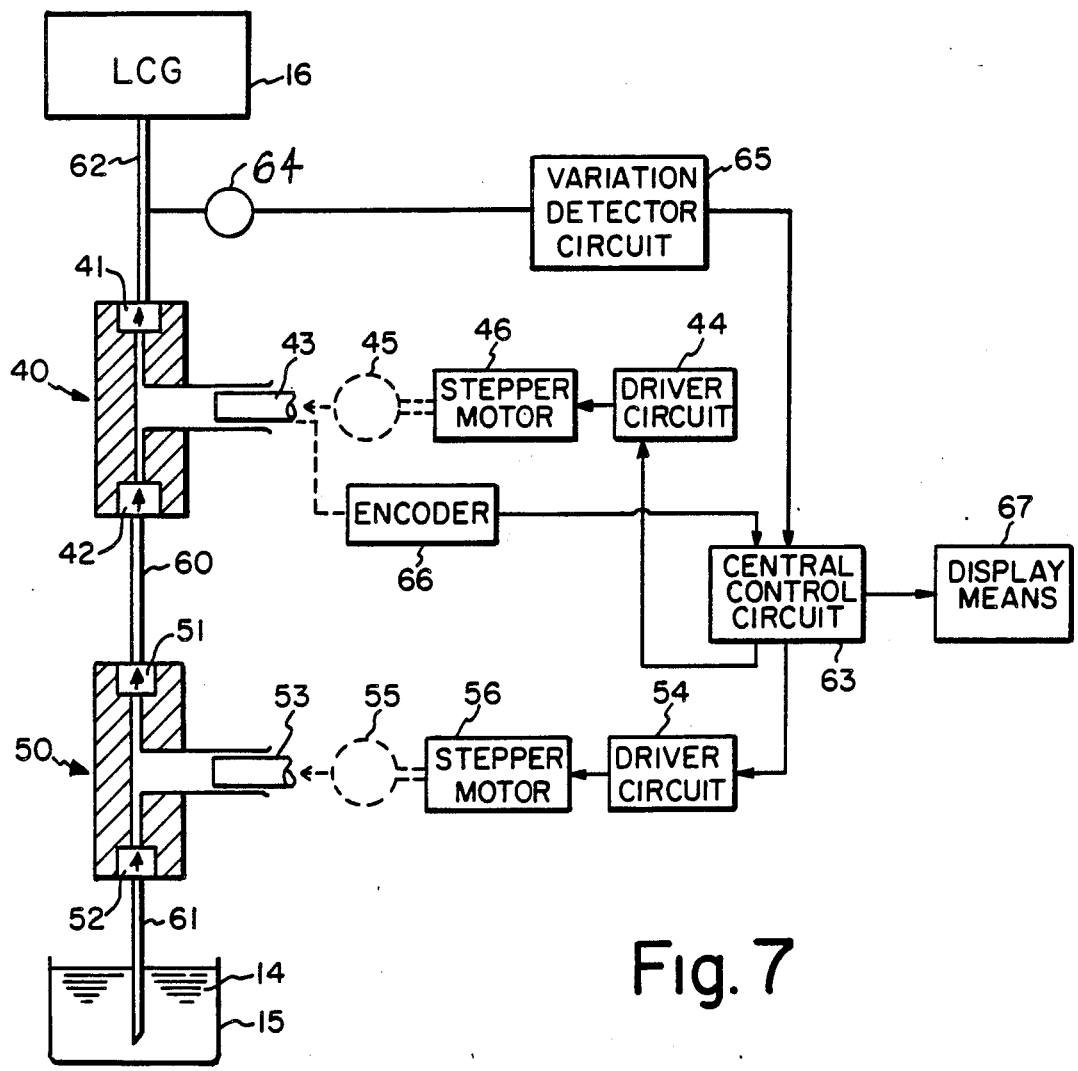
FIG. 7 is a block diagram of a two-stage pump assembly according to the invention.

Referring to FIG. 7, there is shown a two-stage pump assembly according to the invention. This assembly has plunger pumps 40 and 50 similar to the pumps shown in FIG. 1. One-way valves 41 and 51 which allow fluid to pass only in the direction indicated by the arrows are mounted at the discharge ports of the pumps 40 and 50, respectively. Other one-way valves 42 and 52 are mounted at the suction ports of the pumps 40 and 50, respectively. The discharge port of the pump 50 is connected to the suction port of the pump 40 by a pipe 60. Thus, the suction port of the pump 50 acts as the suction port of the whole pump assembly. Liquid 14 contained in liquid reservoir 15 is drawn into the pump via a pipe 61. The discharge port of the pump 40 serves as the discharge port of the whole pump assembly, and is connected via a pipe 62 with the separation column of liquid chromatograph 16. The pumps 40 and 50 have plungers 43 and 53, respectively, which are driven in substantially the same manner as the plungers shown in FIG. 1. More specifically, the plunger 43 has a roller (not shown) attached to its front end, and this roller always abuts against a cam 45 mounted to the shaft of a stepper motor 46. Similarly, a roller (not shown) is mounted to the front end of the plunger 53, and is maintained in abutting engagement with a cam 55 mounted to the shaft of a second stepper motor 56. The motors 46 and 56 are controlled respectively by motor driver circuits 44 and 54, which, in turn, are controlled by control signals from a central control circuit 63.

In the pump assembly shown in FIG. 7, the cylinders of the outlet pump 40 and inlet pump 50 have the same diameter, but it is possible to make the maximum flow rate of the inlet pump 50 larger than the maximum flow rate of the outlet pump 40. A pressure sensor 64 is installed in the pipe 62 to detect the delivery pressure. The output signal from the sensor 64 is fed to a variation detector circuit 64, where the D.C. component of the signal is removed. The output signal from the variation detector circuit 65 is applied to the central control circuit 63. The position of the plunger 43 is converted into an electrical signal by an encoder 66. The output signal from the encoder 66 is also applied to the central control circuit 63. A display means 67 is connected to the central control circuit 63 so that the output from the variation detector circuit 65 may be displayed on it in synchronism with the output from the encoder 66.

Figure 8:
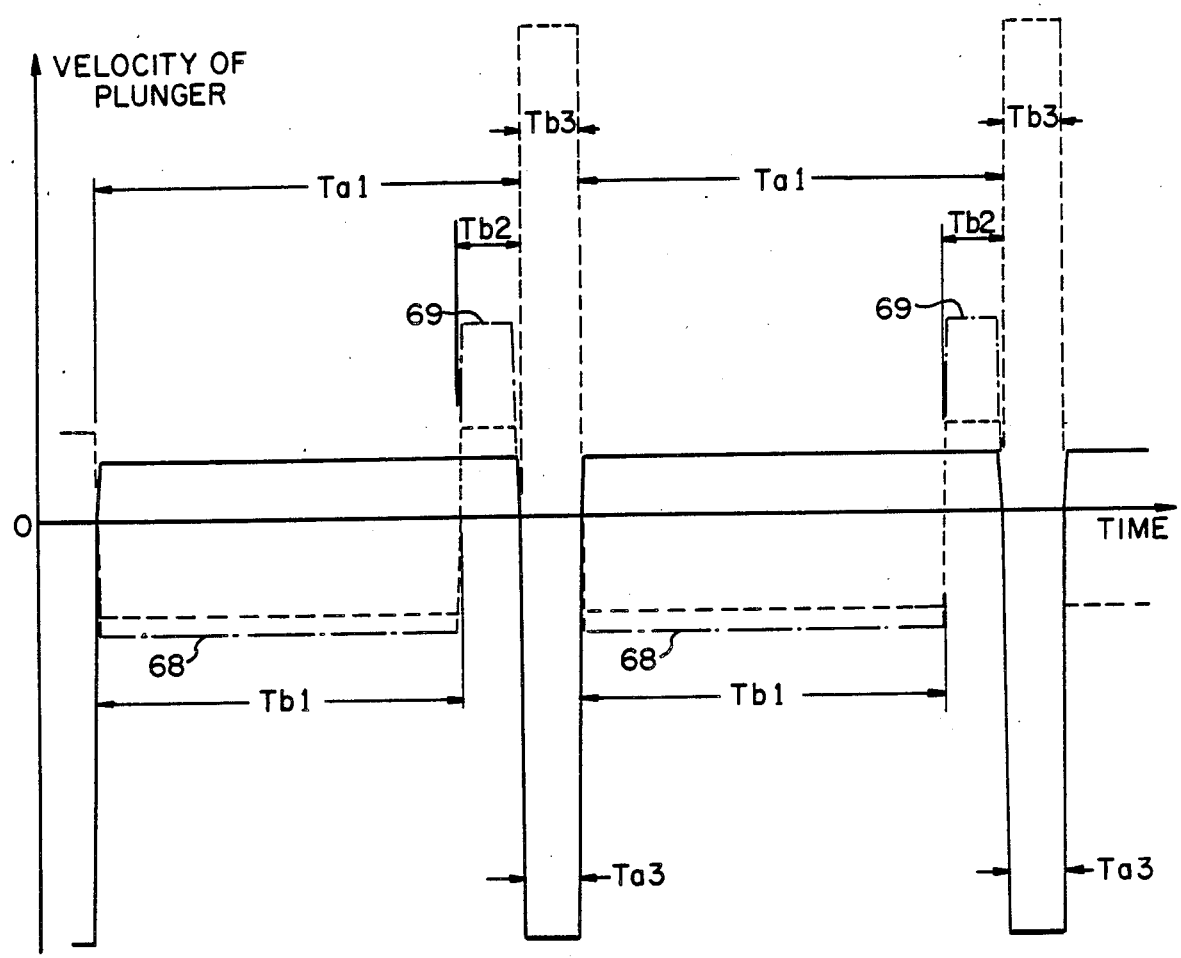
FIG. 8 is a diagram for illustrating the operation of the assembly shown in FIG. 7.

FIG. 8 illustrates the manner in which the pump assembly shown in FIG. 7 is operated under the control of the central control circuit 63. In the diagram of FIG. 8, the velocities of the moving plungers are plotted on the vertical axis and time on the horizontal axis. The movement of the plunger 43 is indicated by the solid line, while the movement of the plunger 53 is indicated by the broken line. Thus, the area of each portion bounded by solid and broken lines indicates the capacity of the pump chamber that is varied by the movement of the plunger. The outlet pump 40 delivers fluid slowly during a relatively long period of $T_{a1}$ and takes in fluid during a short period of $T_{a3}$. Inversely, the inlet pump 50 fills slowly during a relatively long period of $T_{b1}$ and delivers quickly during a short period of $T_{b3}$ which is equal to the period $T_{a3}$. The valves 42 and 51 open only during the periods $T_{a3}$ and $T_{b3}$, respectively. The outlet pump 40 acts to deliver fluid from the whole pump assembly. The inlet pump 50 performs the filling function of the whole pump assembly. The inlet pump 50 preliminarily compresses fluid during period $T_{b2}$ between the periods $T_{b1}$ and $T_{b3}$ until the pressure inside the chamber of the inlet pump 50 reaches the pressure inside the chamber of the outlet pump 40, i.e., the delivery pressure. Of course, the valves 42 and 51 are kept closed during the period $T_{b3}$. The following relations hold between the periods of the strokes:

$$T_{a1} = T_{b1} + T_{b2}, \ T_{a3} = T_{b3}, \ T_{a1} > T_{a3} \ T_{b1} > T_{a3}$$

When the inlet pump 50 is in the filling stroke for the precompression, liquid is supplied from the reservoir 15 at a generally low pressure, or the atmospheric pressure. Therefore, if the pump 50 fills quickly, a cavitation tends to occur inside the chamber or on the valves, producing air bubbles. Then, the pump will not operate regularly. Hence, it is desired that the inlet pump 50 fill very slowly as shown in FIG. 8. On the other hand, the outlet pump 40 is used for measurement, and the displacement stroke of the pump 40 is substantially the displacement stroke of the whole pump assembly. Accordingly, it is desired to make the emptying stroke of the outlet pump 40 longer than the filling stroke, keeping the flow rate constant. During the filling stroke of the outlet pump 40, the compressed fluid is drawn from the pump 50 into the pump 40 via the valves 51 and 42 and so the rapid filling operation in a short time hardly causes cavitation.

The operation of the novel pump assembly constructed as described above is now described. It is to be understood that the cams of the conventional system rotate in one direction. In contrast, in the novel assembly, the cams are rotated back and forth within 360°. The novel assembly is similar to the conventional system shown in FIG. 1 except in these respects. Data indicating a desired flow rate is first entered into the central control circuit 63. Then, the circuit 63 determines the rotational velocity of the cam 45 and the angular range within which the cam swings back and forth, according to the flow rate, the cam 45 acting on the pump 40. The central control circuit 63 then delivers a control signal to the driver circuit 44 to control the operation of the cam 45 in such a way that if the flow rate assumes a large value, the angular range within the cam 45 swings back and forth, hence the period $T_{a1}$ of the displacement stroke and the period $T_{a3}$ of the filling stroke, is extended or the rotational velocity is increased. In this way, the cam is swung right and left repeatedly within the selected angular range. During this operation, the plunger 43 is moved slowly to the left and quickly to the right. This movement of the plunger 43 is monitored by the encoder 66 that converts the position of the plunger into an electrical signal. The output signal from the encoder 66 is supplied to the central control circuit 63, which produces trigger and control signals to the driver circuit 54 in synchronism with the movement of the plunger 43 to initiate the filling and emptying strokes using the plunger 53 and to cause the plunger 53 to move slowly to the right and quickly to the left. After completing one filling stroke, the pump 50 goes to its next stroke of precompression at an instant that is controlled by presetting the period $T_{b1}$ of the filling stroke.

Figure 9A:
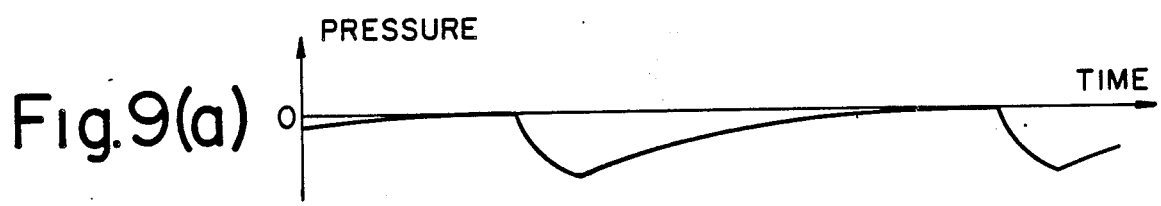
FIGS. 9(a), 9(b) and 9(c) shows graphs for illustrating the operation of the assembly shown in FIG. 7.
Figure 9B:
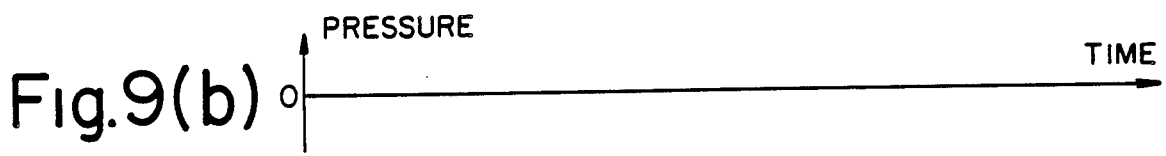
Figure 9C:
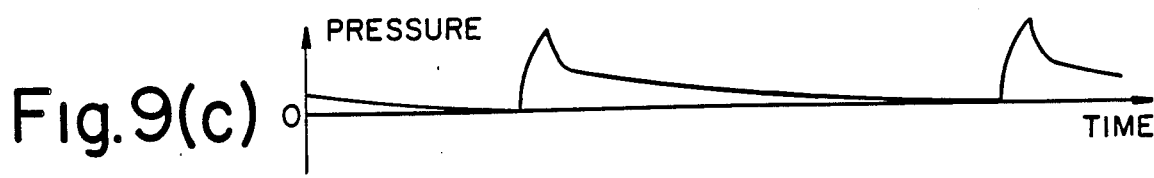

The central control circuit 63 to which the output from the variation detector circuit 65 is applied monitors variations in the pressure inside the pipe 62 in synchronism with the output from the encoder 66. These variations are presented on the display means 67, for example, as shown in FIG. 9. When the pressure characteristic is inclined upwardly to the right as shown in FIG. 9(a), the precompression made by the pump 50 is excessive. When it is inclined downwardly to the right as shown in FIG. 9(c), the precompression is not sufficient. When it is horizontal as shown in FIG. 9(b), the precompression is adequate. When the central control circuit 63 detects the condition shown in FIG. 9(a), it causes the motor driver circuit 54 to increase the velocity of the plunger 53 during the periods $T_{b1}$ and $T_{b2}$, for augmenting the precompression. In this way, velocities indicated by the broken lines in FIG. 8 change to velocities indicated by dot-and-dash lines 68 and 69. Inversely, when the condition shown in FIG. 9(c) is detected, the control circuit 63 instructs the driver circuit 54 to decrease the velocity of the plunger 53 during the periods $T_{b1}$ and $T_{b2}$, for obtaining the condition shown in FIG. 9(b). Although control operations are carried out in this way, the following conditions are invariably satisfied regarding FIG. 8:

(1) The area bounded by both the solid line and the time axis during the period $T_{a1}$ is equal to the area bounded by both the solid line and the time axis during the period $T_{a2}$.

(2) The area bounded by both the broken line and the time axis during the period $T_{b1}$ is equal to the sum of the area bounded by both the broken line and the time axis during the period $T_{b2}$ and the area bounded by both the broken line and the time axis during the period $T_{b3}$.

(3) The delivery of the pump assembly during the period $T_{a3}$ is equal to the difference between the area bounded by both the broken line and the time axis during the period $T_{b3}$ and the area bounded by both the solid line and the time axis during the period $T_{a3}$.

The pump assembly may have a pressure relief valve (not shown) between the discharge valve 51 and the pump 50 and the suction valve 42 of the pump 40, in addition to the structure for controlling the precompression made by the pump 50. More specifically, the pump 50 is so set as to precompress fluid somewhat excessively. The relief valve may be actuated under the control of the central control circuit 63 when the pressure inside the chamber of the pump 50 exceeds the pressure inside the chamber of the pump 40.

Figure 10:
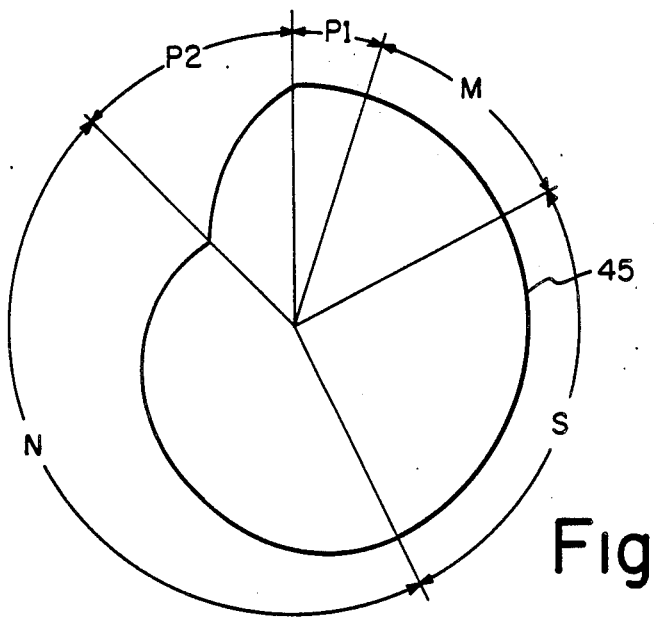
FIG. 10 shows the profile of the cams used in the assembly shown in FIG. 7.
Figure 11:
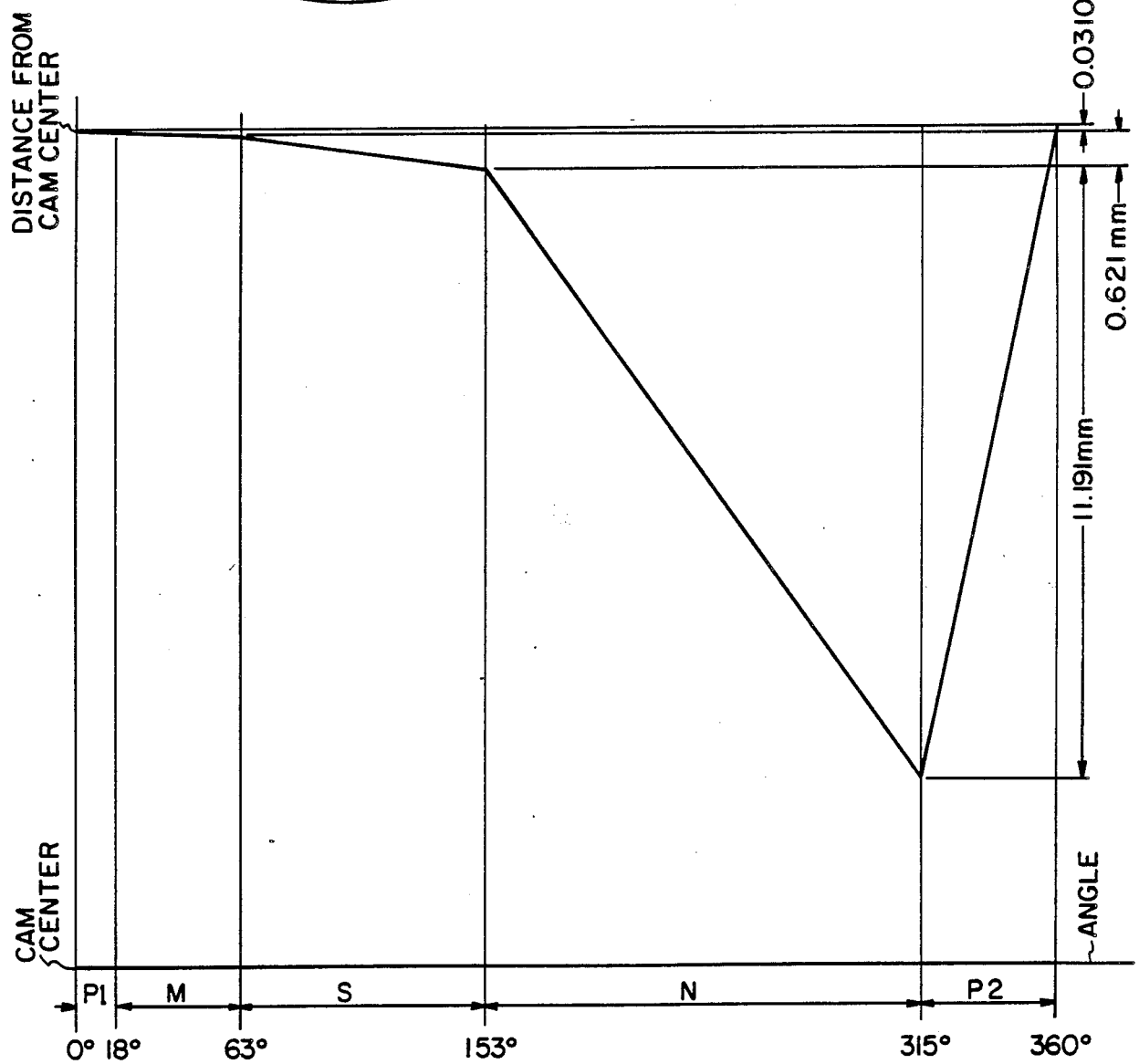
FIG. 11 is an expanded view of the cam profile shown in FIG. 10.

FIG. 10 shows the profile of the cams 45 and 55 used in the assembly shown in FIG. 7. FIG. 11 is an expanded view of the cam profile in terms of the angular distance from the center of the shown cam to its periphery at which it comes into contact with the roller at the front end of the plunger 43 or 53. The cam profile is shown to have five angular ranges P1, M, S, N, and P2. Analytical regions, variable capacity of the pump chamber, and the stroke of the plunger correspond to the angular ranges in the manner listed below.

| P1 | play | (0 to 18°) | 0 μm/18° |
|---|---|---|---|
| M | microanalysis | (18 to 63°) | 31 μm/45° |
| S | semimicroanalysis | (63 to 153°) | 621 μm/90° |
| N | macroanalysis | (153 to 315°) | 11191 μm/162° |

-continued

| P2 | play | (315 to 360°) | 11843 μm/45° |
|---|---|---|---|

The stepper motors 46 and 56 make a full revolution of 360° by receiving 500 pulses. At least 30 pulses per minute are needed to maintain the delivery from the pump smooth. The cam is rotated clockwise and counterclockwise by the reversible stepper motors within any of the angular ranges M, S, and N. The plunger 43 is translated within the cylinder of the pump 50, the cylinder having a diameter of 3 mm. The minimum flow rates achievable in the microanalysis M, the semimicroanalysis S, and the macroanalysis N are 0.05955 μl/min., 0.5955 μl/min., and 5.955 μl/min., respectively.

The central control circuit 63 shown in FIG. 7 selects one of the three angular ranges according to the flow rate entered, and drives the pump within that angular range. The inlet pump 50 is required to deliver fluid at a larger flow rate than the outlet pump 40. Where the cam 55 is identical in profile with the cam 45, it is necessary to rotate the cam 55 over two or more of the angular ranges. In this manner, the novel pump assembly alone is capable of covering a very wide range of flow rates.

We claim:

1. In a two-stage pump assembly having two pumps A and B and a control means for controlling the operation of each pump in such a way that the pump assembly delivers fluid, each of the two pumps having a cylinder constituting a chamber, a plunger fitted in the cylinder and making reciprocating motion to vary the capacity of the chamber, and one-way valves disposed at the suction port and at the discharge port, respectively, of the chamber, the improvement comprising:

(A) the suction port of the pump A is connected to the discharge port of the pump B, and the discharge port of the pump A and the suction port of the pump B act as the discharge port and the suction port, respectively, of the whole pump assembly;

(B) said means for controlling causing the suction stroke of the pump B (period $T_{b1}$) to start simultaneously with the discharge stroke of the pump A (period $T_{a1}$), and the discharge of the pump B (period $T_{b3}$) to start simultaneously with the suction stroke of the pump A (period $T_{a3}$);

(C) said means for controlling causing a compression stroke in pump B during a period of $T_{b2}$ between the suction stroke and the discharge of the pump B;

(D) the periods being so set as to satisfy the following reactions:

$$T_{a1} = T_{b1} + T_{b2}, \ T_{a3} = T_{b3}, \ T_{a1} > T_{a3}, \ T_{b1} > T_{a3};$$

and, (E) wherein said means for controlling each pump comprises
  (i) two stepper motors each having a rotating output shaft and the capability of causing rotation of the shaft in either direction,
  (ii) cams fixed to each rotating shaft for bearing upon followers attached to the exposed ends of each plunger respectively, and
  (iii) said stepper motors being controlled to rotate back and forth within an angular range controlled according to the desired flow rate.

2. In a two-stage pump assembly having two pumps A and B and a control means for controlling the opration of each pump in such a way that the pump assembly delivers fluid, each of the two pumps having a cylinder constituting a chamber, a plunger fitted in the cylinder and making reciprocating motion to vary the capacity of the chamber, and one-way valves disposed at the suction port and at the discharge port, respectively, of the chamber, the improvement comprising:

(A) the suction port of the pump A is connected to the discharge port of the pump B, and the discharge port of the pump A and the suction port of the pump B act as the discharge port and the suction port, respectively, of the whole pump assembly;

(B) said means for controlling causing the suction stroke of the pump B (period $T_{b1}$) to start simultaneously with the discharge stroke of the pump A (period $T_{a1}$), and the discharge of the pump B (period $T_{b3}$) to start simultaneously with the suction stroke of the pump A (period $T_{a3}$);

(C) said means for controlling causing a compression stroke in pump B during a period of $T_{b2}$ between the suction stroke and the discharge of the pump B;

(D) the periods being so set as to satisfy the following relations:

$$T_{a1} = T_{b1} + T_{b2}, \; T_{a3} = T_{b3}, \; T_{a1} > T_{a3}, \; T_{b1} > T_{a3}$$

(E) there being provided means for detecting variations in the pressure at the discharge port of the pump A and for displaying the resultant signal in synchronism with the operation of the pump A; and, (F) wherein said means for controlling each pump comprises
  (i) two stepper motors each having a rotating output shaft and the capability of causing rotation of the shaft in either direction,
  (ii) cams fixed to each rotating shaft for bearing upon followers attached to the exposed ends of each plunger respectively, and
  (iii) said stepper motors being controlled to rotate back and forth within an angular range controlled according to the desired flow rate.

3. In a two-stage pump assembly having two pumps A and B and a control means for controlling the operation of each pump in such a way that the pump assembly delivers fluid, each of the two pumps having a cylinder constituting a chamber, a plunger fitted in the cylinder and making reciprocating motion to vary the capacity of the chamber, and one-way valves disposed at the suction port and at the discharge port, respectively, of the chamber, the improvement comprising:

(A) the suction port of the pump A is connected to the discharge port of the pump B, and the discharge port of the pump A and the suction port of the pump B act as the discharge port and the suction port, respectively, of the whole pump assembly;

(B) said means for controlling causing the suction stroke of the pump B (period $T_{b1}$) to start simultaneously with the discharge stroke of the pump A (period $T_{a1}$), and the discharge of the pump B (period $T_{b3}$) to start simultaneously with the suction stroke of the pump A (period $T_{a3}$);

(C) said means for controlling causing a compression stroke in pump B during a period of $T_{b2}$ between the suction stroke and the discharge of the pump B;

(D) the periods being so set as to satisfy the following relations:

$$T_{a1} = T_{b1} + T_{b2}, \; T_{a3} = T_{b3}, \; T_{a1} > T_{a3}, \; T_{b1} > T_{a3}$$

(E) means for detecting the variation in the pressure at the discharge port of the pump A that occurs during each stroke and for controlling the angular velocity of a stepper motor driving the plunger of the pump B during the periods $T_{b1}$ and $T_{b2}$ whereby variations in the pressure at the discharge port of the pump A are reduced; and, (F) wherein said means for controlling each pump comprises
  (i) two stepper motors each having a rotating output shaft and the capability of causing rotation of the shaft in either direction,
  (ii) cams fixed to each rotating shaft for bearing upon followers attached to the exposed ends of each plunger respectively, and
  (iii) said stepper motors being controlled to rotate back and forth within an angular range controlled according to the desired flow rate.

4. In a two-stage pump assembly as set forth in claim 3, the further improvement comprising means for detecting a signal indicative of the position of the plunger in pump A and means for controlling the angular velocity of the stepper motor driving the plunger of pump B in response to the pressure variation signal and the position signal.

5. In a two-stage pump assembly as set forth in claims 1, 2 or 3, the further improvement wherein the profile of each cam is so made that the distance traveled by each plunger whenever the corresponding stepper motor rotates a unit step angle varies among different angular ranges.

* * * * *

UNITED STATES PATENT AND TRADEMARK OFFICE
CERTIFICATE OF CORRECTION

PATENT NO. : 4,681,513

DATED : July 21, 1987

INVENTOR(S) : Toshinori Saito et al.

It is certified that error appears in the above-identified patent and that said Letters Patent is hereby corrected as shown below:

Column 5 Line 46 "64" should read —65—.

Column 6 Line 51 After "within" insert —which—.

Claim 1 Column 8 Line 55 "$I_{a1}$" should read —$T_{a1}$—.

Claim 2 Column 9 Lines 2 & 3 "opration" should read —operation—.

Signed and Sealed this

Seventeenth Day of November, 1987

Attest:

DONALD J. QUIGG

Attesting Officer

Commissioner of Patents and Trademarks